(12) United States Patent
Govaerts et al.

(10) Patent No.: US 9,127,010 B2
(45) Date of Patent: Sep. 8, 2015

(54) PREPARATION OF 13-CYCLOHEXYL-3-METHOXY-6-[METHYL-(2-{2-[METHYL-(SULPHAMOYL)-AMINO]-ETHOXY}-ETHYL)-CARBAMOYL]-7H-INDOLO-[2,1-A]-[2]-BENZAZEPINE-10-CARBOXYLIC ACID

(75) Inventors: Tom Cornelis Hortense Govaerts, Betekom (BE); Jean-Pierre-Andre Marc Bongartz, Turnhout (BE); Patrick Hubert J. Nieste, Westerlo (BE)

(73) Assignee: Janssen Sciences Ireland UC, Little Island, Co. Cork (IE)

( * ) Notice: Subject to any disclaimer, the term of this patent is extended or adjusted under 35 U.S.C. 154(b) by 95 days.

(21) Appl. No.: 13/805,607

(22) PCT Filed: Jun. 24, 2011

(86) PCT No.: PCT/EP2011/060606
§ 371 (c)(1),
(2), (4) Date: Dec. 19, 2012

(87) PCT Pub. No.: WO2011/161232
PCT Pub. Date: Dec. 29, 2011

(65) Prior Publication Data
US 2013/0102777 A1   Apr. 25, 2013

(30) Foreign Application Priority Data
Jun. 24, 2010   (EP) .................................... 10167221

(51) Int. Cl.
C07D 487/04 (2006.01)
C07D 223/14 (2006.01)
C07C 307/06 (2006.01)

(52) U.S. Cl.
CPC ............ *C07D 487/04* (2013.01); *C07C 307/06* (2013.01); *C07D 223/14* (2013.01)

(58) Field of Classification Search
CPC .................................................... C07D 487/04
USPC ....................................................... 540/576
See application file for complete search history.

(56) References Cited

U.S. PATENT DOCUMENTS

| | | | |
|---|---|---|---|
| 5,807,876 | A | 9/1998 | Armistead et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 8,921,355 | B2 | 12/2014 | Vendeville et al. |
| 2007/0270405 | A1 | 11/2007 | Bender et al. |
| 2007/0270406 | A1 | 11/2007 | Gentles et al. |
| 2008/0146537 | A1 | 6/2008 | Bender et al. |
| 2014/0107101 | A1 | 4/2014 | Vendeville et al. |

FOREIGN PATENT DOCUMENTS

| | | |
|---|---|---|
| WO | 9740028 A1 | 10/1997 |
| WO | 9840381 A1 | 9/1998 |
| WO | 0056331 A1 | 9/2000 |
| WO | 0219369 A2 | 3/2002 |
| WO | 2006020082 A1 | 2/2006 |
| WO | 2007026024 A2 | 3/2007 |
| WO | 2007033032 A1 | 3/2007 |
| WO | 2007054741 A1 | 5/2007 |
| WO | 2007092000 A1 | 8/2007 |
| WO | WO 2007/140200 A2 | 12/2007 |
| WO | 2008075103 A1 | 6/2008 |
| WO | 2009010783 A1 | 1/2009 |
| WO | 2010003658 A1 | 1/2010 |

OTHER PUBLICATIONS

Consensus Development Panel, National Institutes of Health Consensus Development Conference Statement: Management of Hepatitis C: 2002, Hepatology, Jun. 2002, S3-S20, vol. 36, No. 5.
Dierynck, et al., Binding Kinetics of Darunavir to Human Immunodeficiency Virus Type 1 Protease Explain the Potent Antiviral Activity and High Genetic Barrier, Journal of Virology, Dec. 15, 2007, pp. 13845-13851, vol. 81, No. 24.
Huang, et al., Olefin Metathesis-Active Ruthenium Complexes Bearing a Nucleophilic Carbene Ligand, The Journal of the American Chemical Society, 1999, p2674-2678, vol. 121.
Kazutaka et al, Discovery of Conformationally Constrained Tetracyclic Compounds as Potent Hepatitis C Virus NS5B RNA Polymerase Inhibitors, Journal of Med Chem, 2006, 6950-6953, 49.
Kim et al, The Burden of Hepatitis C in the United States, Hepatology, 2002, S30-S34, vol. 36, No. 5, s1.
Kingsbury et al, A Recyclable Ru-Based Metathesis Catalyst, The Journal of the American Chemical Society, 1999, p. 791-799, vol. 121.
Krieger, et al, Enhancement of Hepatitis C Virus RNA Replication by Cell Culture, Journal of Virology, May 1, 2001, 4614-1624, 75-10, DE.
Lohmann, et al., Replication of Subgenomic Hepatitis C Virus RNAs in a Hepatoma Cell Line, Science, 1999, pp. 110-113, vol. 285.
Miller et al, Application of Ring-Closing Metathesis to the Synthesis of Rigidified Amino Acids and Peptides, The Journal of the American Chemical Society, 1996, p9606-9614, vol. 118.
Pauwels, et al., Binding-Site Identification and Genotypic Profiling of Hepatitis C Virus Polymerase Inhibitors, Journal of Virology, 2007, pp. 6909-6919, vol. 81, No. 13.

*Primary Examiner* — Brenda Coleman
(74) *Attorney, Agent, or Firm* — Andrea Jo Kamage

(57) ABSTRACT

The present invention relates to an improved method for the preparation of 13-cyclohexyl-3-methoxy-6-[methyl-(2-{2-[methyl-(sulphamoyl)-amino]-ethoxy}-ethyl)-carbamoyl]-7H-indolo-[2,1-a]-[2]-benzazepine-10-carboxylic acid. The present invention also relates to a new compound, namely tert-butyl (methyl-{2-[2-(methylamino)-ethoxy]-ethyl}-sulphamoyl)-carbamate, used in this improved method.

7 Claims, No Drawings

PREPARATION OF 13-CYCLOHEXYL-3-METHOXY-6-[METHYL-(2-{2-[METHYL-(SULPHAMOYL)-AMINO]-ETHOXY}-ETHYL)-CARBAMOYL]-7H-INDOLO-[2,1-A]-[2]-BENZAZEPINE-10-CARBOXYLIC ACID

This application is a national stage application of PCT/EP2011/060606, filed Jun. 24, 2011, which claims priority benefit of Application No. EP 10167221.0 filed Jun. 24, 2010. The complete disclosures of the aforementioned related patent applications are hereby incorporated herein by reference for all purposes.

The present invention relates to an improved method for the preparation of 13-cyclohexyl-3-methoxy-6-[methyl-(2-{2-[methyl-(sulphamoyl)-amino]-ethoxy}-ethyl)-carbamoyl]-7H-indolo-[2,1-a]-[2]-benzazepine-10-carboxylic acid. The present invention also relates to a new compound, namely tert-butyl (methyl-{2-[2-(methylamino)-ethoxy]-ethyl}-sulphamoyl)-carbamate, used in this improved method.

Compound 'A'

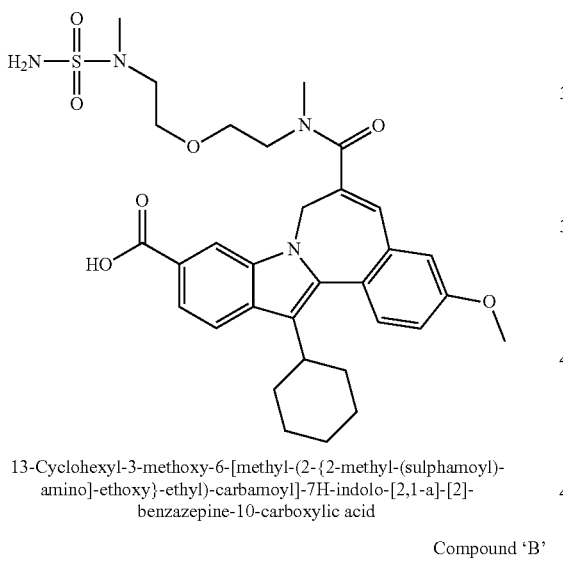

13-Cyclohexyl-3-methoxy-6-[methyl-(2-{2-methyl-(sulphamoyl)-amino]-ethoxy}-ethyl)-carbamoyl]-7H-indolo-[2,1-a]-[2]-benzazepine-10-carboxylic acid Compound 'B' tert-Butyl (methyl-{2-[2-(methylamino)-ethoxy]-ethyl}-sulphamoyl)-carbamate

WO 2010/003658 describes some macrocyclic indoles that can be used as inhibitors of the hepatitis C virus. The synthesis of 13-cyclohexyl-3-methoxy-6-[methyl-(2-{2-[methyl-(sulphamoyl)-amino]-ethoxy}-ethyl)-carbamoyl]-7H-indolo-[2,1-a]-[2]-benzazepine-10-carboxylic acid (Compound 'A') was described there on pages 38 and 39 (see Compound 1e) as a three-step synthesis, giving an overall yield of 62%.

Step 1

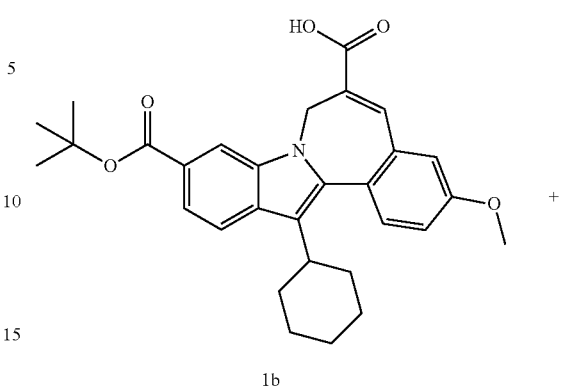

1b

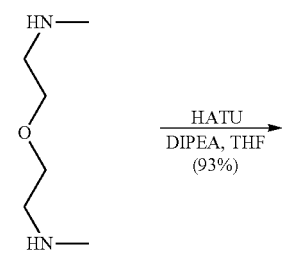

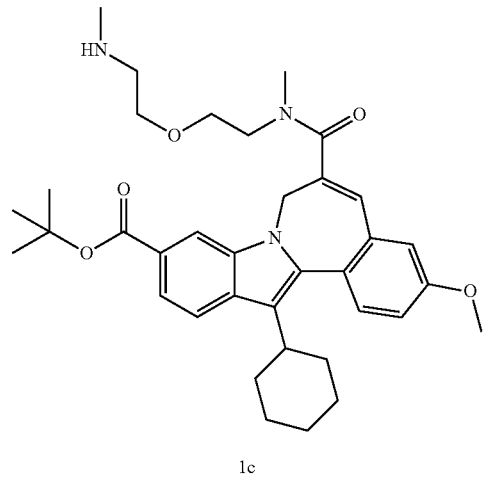

1c

Step 2

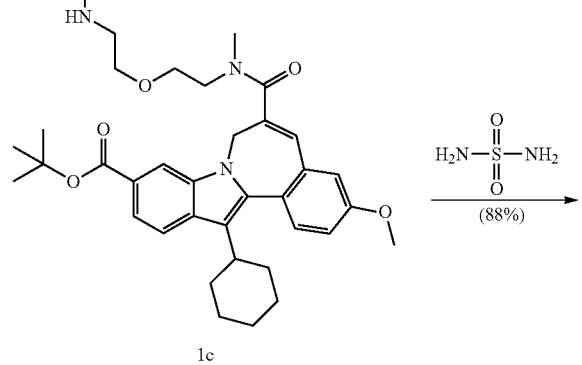

1c

-continued

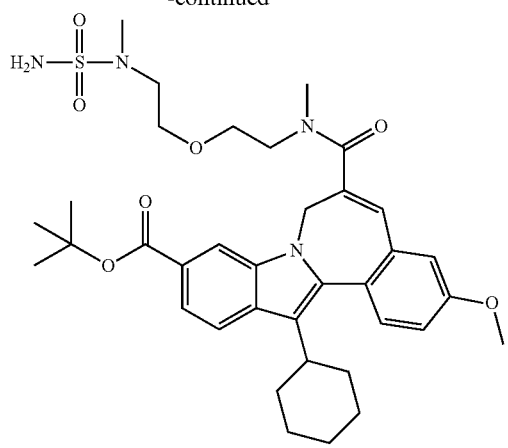

1d

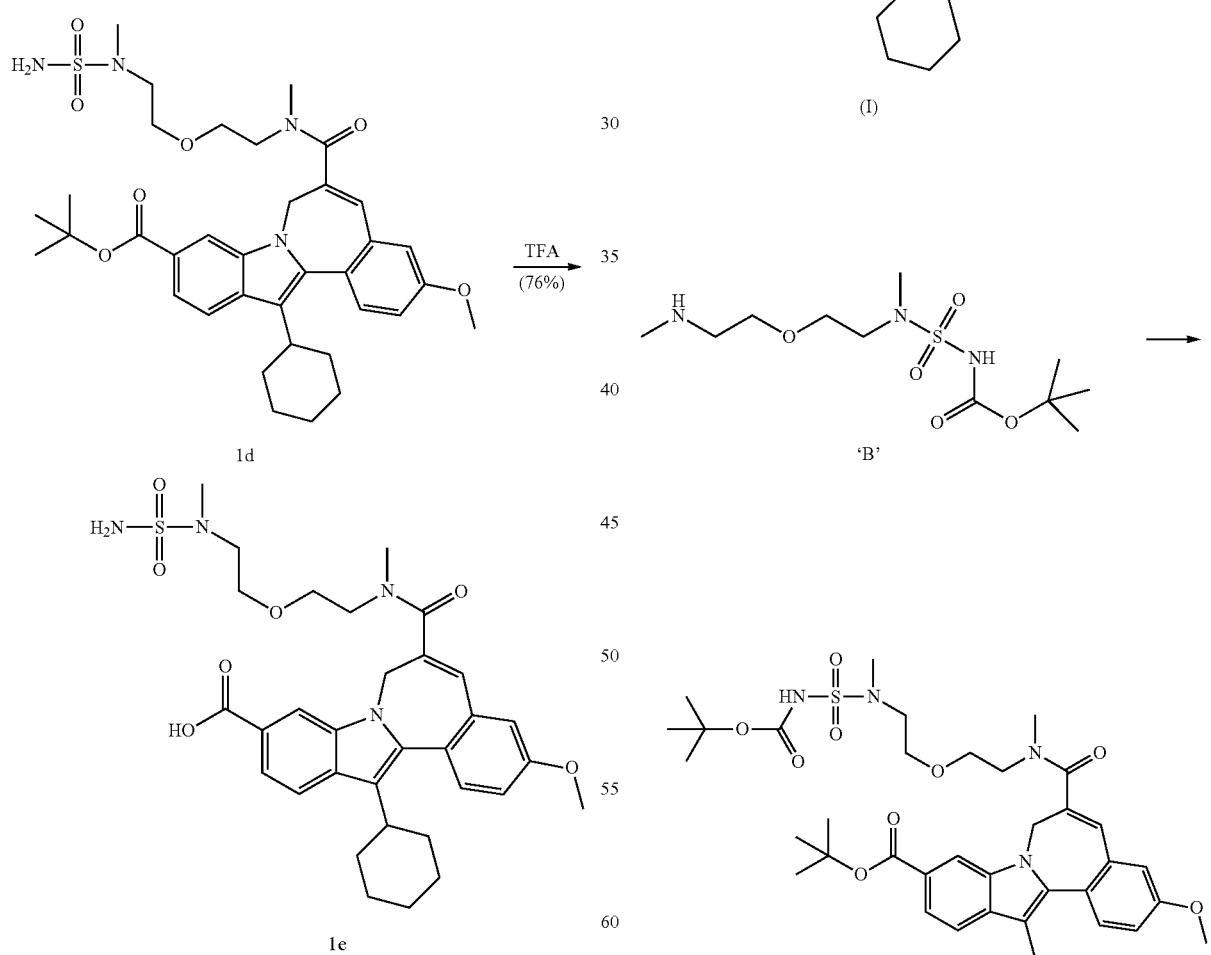

1d

1e

The aim of the present invention is to provide an improved method for the synthesis of 13-cyclohexyl-3-methoxy-6-[methyl-(2-{2-[methyl-(sulphamoyl)-amino]-ethoxy}-ethyl)-carbamoyl]-7H-indolo-[2,1-a]-[2]-benzazepine-10-carboxylic acid (Compound 'A') that is easier to carry out and is more efficient than the method known so far.

The present invention achieves this aim by providing an improved method for the preparation of 13-cyclohexyl-3-methoxy-6-[methyl-(2-{2-[methyl-(sulphamoyl)-amino]-ethoxy}-ethyl)-carbamoyl]-7H-indolo-[2,1-a]-[2]-benzazepine-10-carboxylic acid ('Compound A'), characterized in that it comprises the following steps:

a) 10-(tert-butoxycarbonyl)-13-cyclohexyl-3-methoxy-7H-indolo-[2,1-a]-[2]-benzazepine-6-carboxylic acid (Compound I) is reacted with tert-butyl (methyl-{2-[2-(methylamino)-ethoxy]-ethyl}-sulphamoyl)-carbamate (Compound 'B') in the presence of a coupling agent in a suitable solvent

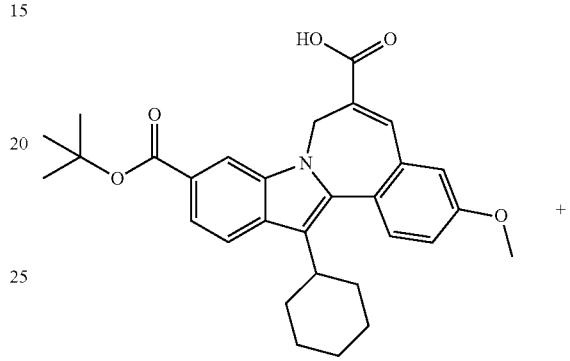

(I)

'B'

(II)

b) and Compound (II) thus obtained is hydrolysed with an acid to prepare Compound 'A'.

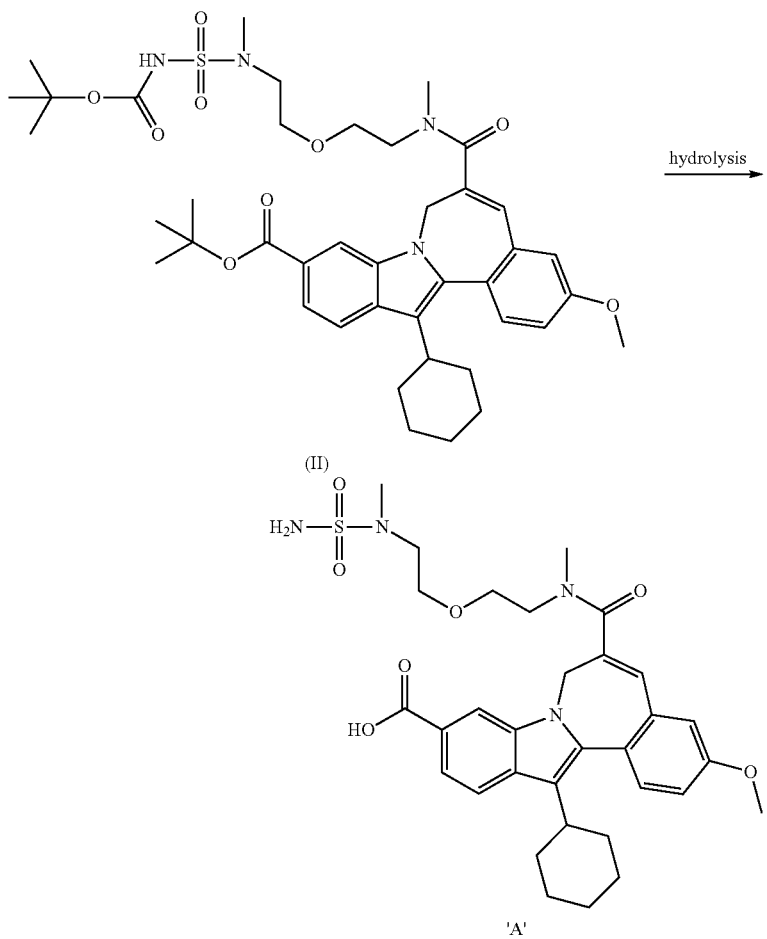

The coupling agent in Step a) is e.g. carbodiimidazole (CDI), dicyclohexylcarbodiimide (DCC), O-(7-azabenztriazolo-1-yl)-1,1,3,3-tetramethyluronium hexafluorophosphate (HATU), bromotri-(pyrrolidino)-phosphonium hexafluorophosphate (PyBrOP), a combination of 1-hydroxybenztriazole hydrate (HOBt.H$_2$O) and 1-ethyl-3-(3-dimethylaminopropyl)-carbodiimide hydrochloride (EDCI).

A suitable solvent in Step a) is e.g. dichloromethane, 2-methyltetrahydrofuran, acetonitrile, acetone, 2-butanone, 4-methyl-2-pentanone, ethyl acetate, isopropyl acetate or toluene.

The hydrolysis in Step b) can be carried out by using trifluoroacetic acid, methanesulphonic acid, hydrogen chloride, hydrogen bromide, para-toluenesulphonic acid, sulphuric acid or phosphoric acid.

Steps a) and b) can be carried out as a two-step synthesis, in which Compound (II) is isolated in Step a) before carrying out Step b), or else Steps a) and b) are conducted as a one-vessel synthesis.

The overall yield obtained in Steps a) and b) is between 86 and 91%, depending on which of the procedures described in Examples 3, 4 and 5 (Experiment B) is used to carry out the new method.

The present invention also relates to a new compound (Compound 'B') with the following formula, and possible acid-addition salts thereof:

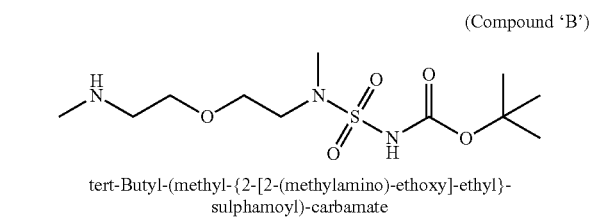 [SMILES: CNCCOCCN(C)S(=O)(=O)NC(=O)OC(C)(C)C]

(Compound 'B')

tert-Butyl-(methyl-{2-[2-(methylamino)-ethoxy]-ethyl}-sulphamoyl)-carbamate

The acid-addition salts of Compound 'B' include the salts that Compound 'B' can form with organic or inorganic acids, such as mineral acids, sulphonic acids, carboxylic acids and phosphorus-containing acids. Examples of salt-forming mineral acids are hydrofluoric acid, hydrochloric acid, hydrobromic acid, hydriodic acid, sulphuric acid, nitric acid, chloric acid, perchloric acid and phosphoric acid. Salt-forming sulphonic acids are toluenesulphonic acid, benzenesulphonic acid, methanesulphonic acid and trifluormethanesulphonic acid. Salt-forming carboxylic acids are formic acid, acetic acid, propionic acid, butanoic acid and the like. Salt-forming dicarboxylic acids are oxalic acid, malonic acid, succinic acid, glutaric acid and the like. Salt-forming hydroxy-acids are glycollic acid, lactic acid, malic acid, tartaric acid, citric acid, mandelic acid and the like. Other salt-forming carboxylic acids are trifluoroacetic acid, benzoic acid, chloroacetic acid, phthalic acid, maleic acid and malonic acid. Phosphorus-containing acids are various phosphono-acids, phosphonic acids and phosphinic acids.

This new Compound 'B' can be synthesized as follows:

Step 1:

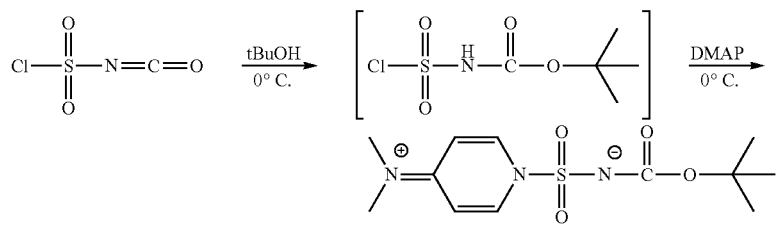

Step 2:

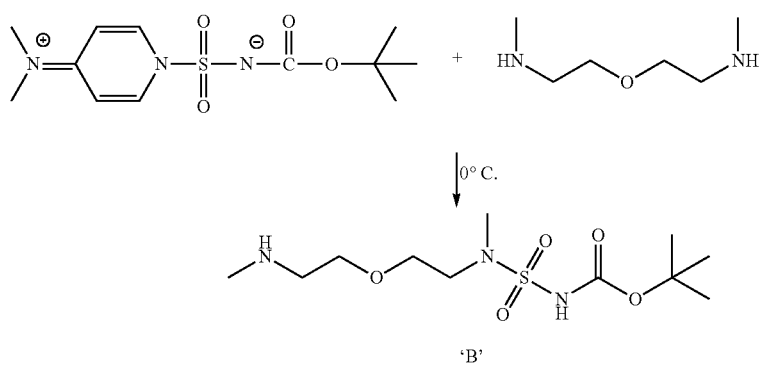

EXPERIMENTAL

The following abbreviations are used here:

A/A: active yield
CDI: carbonyldiimidazole
CSI: chlorosulphonyl isocyanate
DBU: 1,8-diaza-bicyclo-[5,4,0]-undecene-7
DIPE: diisopropyl ether
DMAP: 4-dimethylaminopyridine
DME: 1,2-dimethoxyethane
DMSO-d6: deuterated dimethylsulphoxide
EDCI: 1-ethyl-3-(3-dimethylaminopropyl)-carbodiimide hydrochloride
F/F: physical yield
HOBt: 1-hydroxybenzotriazole hydrate
iPrOAc: isopropyl acetate
LC: liquid chromatography
MeCN: acetonitrile
MEK: methyl ethyl ketone (2-butanone)
MeTHF: 2-methyltetrahydrofuran
MeSO3H: methanesulphonic acid
MIK: methyl isopropyl ketone
MTBE: methyl tert-butyl ether
NMR: nuclear magnetic resonance
tBuOH: tert-butanol
tBOC: tert-butoxycarbonyl
THF: tetrahydrofuran Example 1

Intermediate (1)

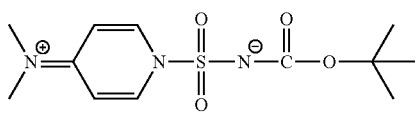

A solution of 8.205 g of chlorosulphonyl isocyanate (58.0 mmol, 1 Eq) in 50 ml of acetonitrile (1 litre/mol) was cooled to −2° C. on an ice/salt bath under nitrogen, using a 500-ml four-neck flask fitted with a thermometer, a magnetic stirrer and a dropping (addition) funnel. A solution of 4.297 g of tert-butanol (58.0 mmol, 1 Eq) in 33 ml of acetonitrile (0.5 l/mol) was added dropwise over 20 minutes, with the temperature remaining below 4° C. Four minutes later (when the temperature had dropped to 1° C.), a solution of DMAP (116.0 mmol, 2 Eq) in 55 ml of acetonitrile (1 litre/mol) was added dropwise over 24 minutes, with the temperature remaining below 5° C.

The solution was allowed to stand for 65 minutes to ensure the best crystallization, with the temperature remaining below 3° C. The white suspension was filtered on a Buchner funnel filter, giving a non-tacky white powder. The precipitate was dried overnight in a drying cabinet at 40° C. under vacuum, which gave 9.465 g of Intermediate (I).

Example 2

Compound 'B'

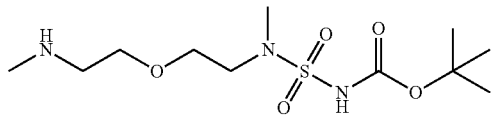

109.1 g (0.825 mol) of 1,5-bis-(methylamino)-3-oxapentane and 1.5 litres of acetonitrile were introduced into a reaction vessel with an inert atmosphere. The resulting solution was cooled to 0° C., and 226 g (0.75 mol) of Intermediate (1) was added to it. The mixture thus obtained was stirred first for 6 hours at 10° C., and then for 3 days at 0° C. The precipitate was filtered off and washed with acetonitrile. After drying at 25° C., Compound 'B' was obtained in a yield of 95 g (40.6%, corrected for purity) in the form of white crystals.

Example 3

Intermediate (2)

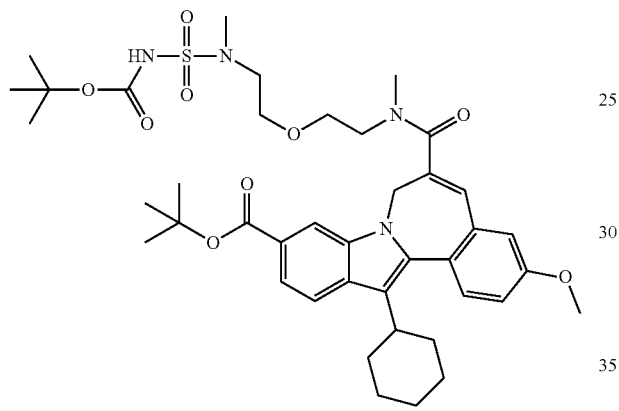

0.400 g (0.82 mmol, 1 Eq) of 10-(tert-butoxycarbonyl)-13-cyclohexyl-3-methoxy-7H-indolo-[2,1-a]-[2]-benzazepine-6-carboxylic acid (called Compound 1b on page 38 of WO 2010/003658), 0.164 g of HOBt (1.07 mmol, 1.3 Eq) and 0.201 g of EDCI (1.07 mmol, 1.3 Eq) were dissolved in 6.5 ml of MeTHF (8 l/mol) in a closed glass flask. The contents of the flask were stirred for 1 hour at room temperature. 0.469 g of Compound 'B' (64.3 wt-%, 0.98 mmol, 1.2 Eq) was then added to the reaction mixture, which was analysed after a reaction time of 18 hours. Analysis by LC indicated that Intermediate (2) had been obtained in a yield of 93.1%.

Example 4

Intermediate (2)

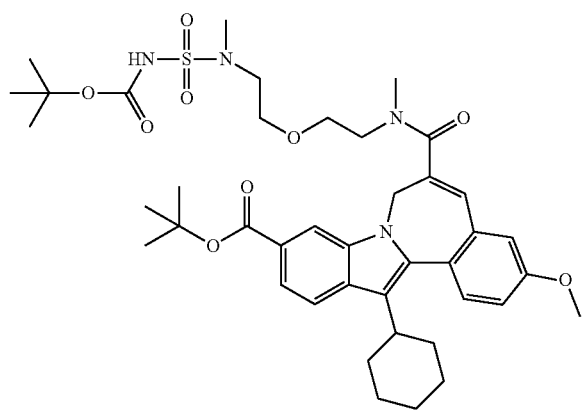

12.00 g (24.61 mmol, 1 Eq) of 10-(tert-butoxycarbonyl)-13-cyclohexyl-3-methoxy-7H-indolo-[2,1-a]-[2]-benzazepine-6-carboxylic acid, 4.92 g of HOBt (31.99 mmol, 1.3 Eq) and 6.03 g of EDCI (31.99 mmol, 1.3 Eq) were introduced into a 100-ml flask and dissolved in 200 ml of MeTHF (8 l/mol). The contents of the flask were stirred for 1 hour at room temperature. Then 11.663 g of Compound 'B' (77.4 wt-%, 29.53 mmol, 1.2 Eq) was added, and the reaction mixture was analysed after a reaction time of 18 hours. Analysis by LC indicated that Intermediate (2) had been obtained in a yield of 98.3%.

The reaction mixture was then extracted and washed first with two 180-ml portions of $H_2O$ (15 l/mol), and then with two 180-ml portions of an $NaHCO_3$ solution (15 l/mol). The organic layer was dried with 2.4 g of $Na_2SO_4$ and filtered, after which the volume of the filtrate obtained was determined. 60 ml of MeTHF was added to make up the volume to 200 ml (8 l/M). Analysis by LC indicated that Intermediate (2) had been obtained in a yield of 93.7%.

Example 5

Compound 'A'

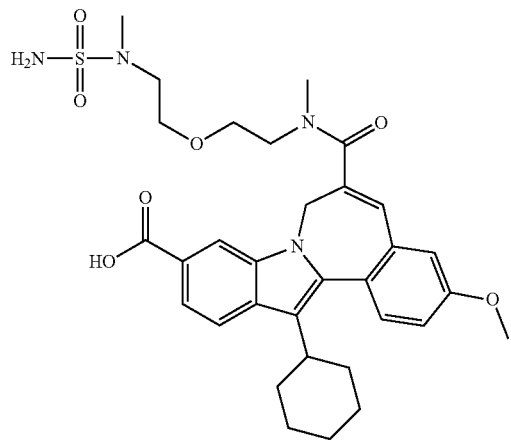

Experiment A

To 13.722 g of Intermediate (2) (16.4 wt-%, 1 Eq, 2.88 mmol) dissolved in MeTHF (8 l/mol) in a 100-ml flask without a nitrogen atmosphere(this solution contained 2.17 wt-% of water), 251 μl of water was added to bring the water content up to 4 wt-%. After the addition of 1.9 ml of $MeSO_3H$ (1 Eq, 28.8 mmol), the reaction mixture was placed on an oil bath heated to 50° C. A sample was taken and analysed after a reaction time of 5 hours. After a reaction time of 22 hours, the reaction mixture was brought to room temperature, and sampled again for analysis. The whole reaction mixture weighed 15.022 g.
Analysis by LC
After 5 hours: 90.1% of Compound 'A'
After 22 hours: 75.4% of Compound 'A'

Experiment B 119.6 g of Intermediate (2) (10.27 wt-%, 15.7 mmol, 1 Eq) was dissolved in MeTHF (8 l/mol) in a reaction vessel with a nitrogen atmosphere. The solution contained 2.21 wt-% of water. 2.81 g of water were added to bring the water content up to 4 wt-%. After the addition of 10.31 ml of $MeSO_3H$ (157 mmol, 10 Eq), the reaction mixture was heated to 50° C. After a reaction time of 5 hours, the reaction mixture was cooled to room temperature, and a sample of it was analysed. The whole reaction mixture weighed 119.6 g.
Analysis by LC
92.7% of Compound 'A'

The invention claimed is:
1. Method for the preparation of 13-cyclohexyl-3-methoxy-6-[methyl-(2-{2-[methyl-(sulphamoyl)-amino]-ethoxy}-ethyl)-carbamoyl]-7H-indolo-[2,1-a]-[2]-benzazepine-10-carboxylic acid (Compound 'A'), comprising steps:
a) reacting 10-(tert-butoxycarbonyl)-13-cyclohexyl-3-methoxy-7H-indolo-[2,1-a]-[2]-benzazepine-6-carboxylic acid (Compound I) with tert-butyl (methyl-{2-[2-(methylamino)-ethoxy]-ethyl}-sulphamoyl)-carbamate (Compound 'B') in the presence of a coupling agent in a suitable solvent, and

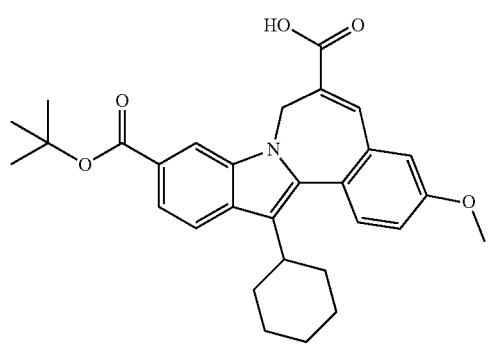

(I)

+

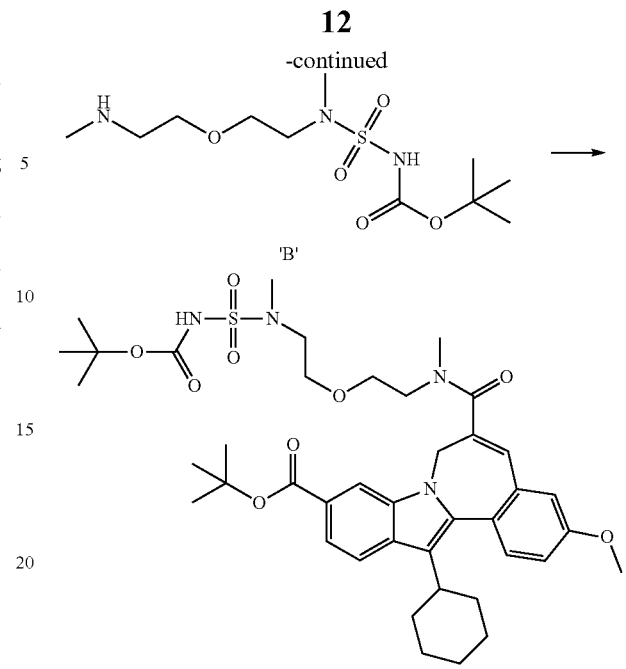

b) hydrolysing Compound (II) thus obtained with an acid, so that Compound 'A' is obtained

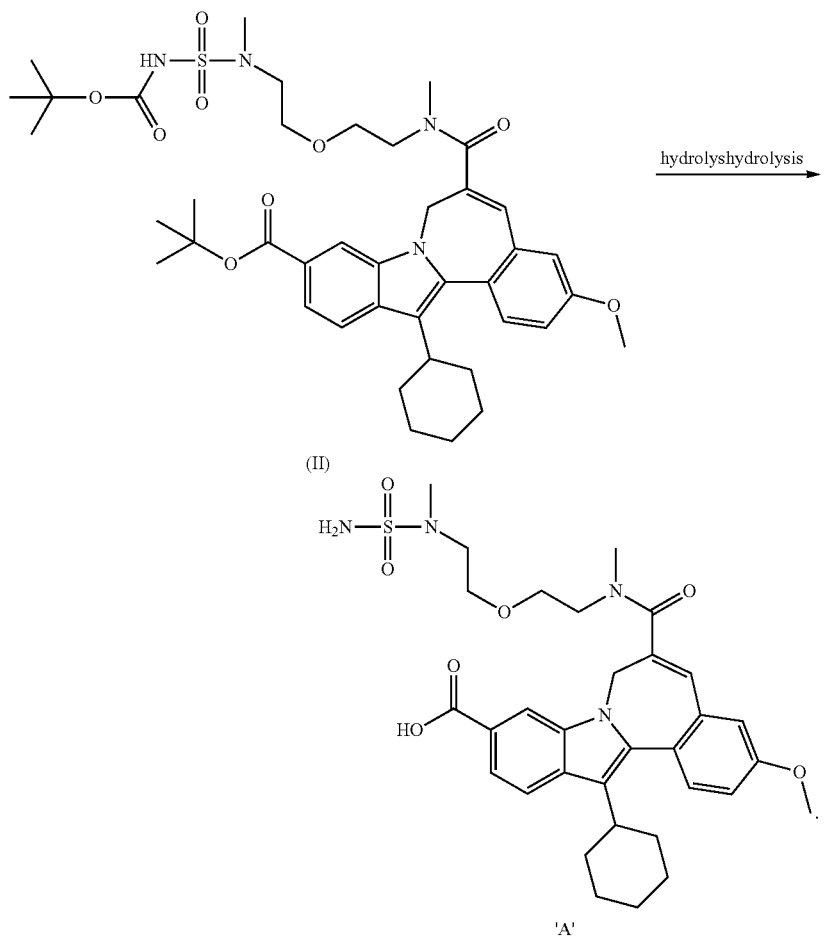

2. Method of claim 1, where steps a) and b) are carried out as a one-vessel synthesis.

3. Method of claim 1, where the coupling agent is selected from the group consisting of: carbodiimidazole (CDI), dicyclohexylcarbodiimide (DCC), O-(7-azabenzotriazole-1-yl)-1,1,3,3-tetramethyluronium hexafluorophosphate (HATU), bromotri-(pyrrolidino)-phosphonium hexafluorophosphate (PyBrOP), and a combination of 1-hydroxybenztriazole hydrate (HOBT.$H_2O$) and 1-ethyl-3-(3-dimethylaminopropyl)-carbodiimide hydrochloride (EDCI).

4. Method of claim 1, where the acid used in step b) is selected from the group consisting of trifluoroacetic acid, methanesulphonic acid, hydrogen chloride, hydrogen bromide, para-toluenesulphonic acid, sulphuric acid and phosphoric acid.

5. Method according to of claim 1, where the preparation is carried out in a nitrogen atmosphere.

6. Method of claim 5, where the solvent used in step a) is 2-methyltetrahydrofuran.

7. Method of claim 6, where the organic acid used in step b) is methanesulphonic acid, the reaction temperature is 50° C., and the duration of the reaction is no longer than 5 hours.

* * * * *